United States Patent
Evenden et al.

(10) Patent No.: US 6,184,219 B1
(45) Date of Patent: *Feb. 6, 2001

(54) COMPOSITION AND METHODS EMPLOYING IT FOR THE TREATMENT OF 5-HT-MEDIATED DISORDERS

(75) Inventors: John Evenden, Wellesley, MA (US); Seth-Olov Thorberg, Strängnäs (SE)

(73) Assignee: Astra Aktiebolag, Sodertalje (SE)

( * ) Notice: Under 35 U.S.C. 154(b), the term of this patent shall be extended for 0 days.

This patent is subject to a terminal disclaimer.

(21) Appl. No.: 09/351,071

(22) Filed: Jul. 9, 1999

Related U.S. Application Data

(63) Continuation-in-part of application No. 08/640,896, filed as application No. PCT/SE96/00526 on Apr. 23, 1996, now Pat. No. 5,962,514.

(30) Foreign Application Priority Data

Apr. 27, 1995 (SE) .................................................. 9501567

(51) Int. Cl.⁷ ........................... A61K 31/35; A61K 31/40
(52) U.S. Cl. ........................... 514/217; 514/357; 514/456
(58) Field of Search ................................... 514/217, 357, 514/456

(56) References Cited

U.S. PATENT DOCUMENTS 5,962,514 * 10/1999 Evenden et al. ..................... 514/456

* cited by examiner

*Primary Examiner*—Frederick Krass
(74) *Attorney, Agent, or Firm*—White & Case LLP

(57) ABSTRACT

The invention relates to a composition comprising a first component (a) which is (R)-5-carbamoyl-8-fluoro-3-N,N-dicyclobutylamino-3,4-dihydro-2H-1-benzopyran in the form of the free base, or a pharmaceutically acceptable salt and/or solvate thereof, and a second component (b) which is (+)-1-[3-(dimethylamino)propyl]-1-(p-fluorophenyl)-5-phthalancarbonitrile in the form of the free base, or a pharmaceutically acceptable salt and/or solvate thereof. The invention is further directed to the preparation of the composition, pharmaceutical formulations containing said composition, and a method of treatment of affective disorders such as mood disorders and anxiety disorders with said composition, as well as a kit containing said composition.

11 Claims, No Drawings

COMPOSITION AND METHODS EMPLOYING IT FOR THE TREATMENT OF 5-HT-MEDIATED DISORDERS

This application is a continuation-in-part of application Ser. No. 08/640,896, filed May 9, 1996, now U.S. Pat. No. 5,962,514 which is a 371 of PCT/SE96/00526, filed Apr. 23, 1996.

FIELD OF THE INVENTION

The present invention relates to a composition which comprises a first component (a) which is (R)-5-carbamoyl-8-fluoro-3-N,N-dicyclobutylamino-3,4-dihydro-2H-1-benzopyran in the form of the free base, or a pharmaceutically acceptable salt and/or solvate thereof, and a second component (b) which is (+)-1-[3-(dimethylamino)propyl]-1-(p-fluorophenyl)-5-phthalancarbonitrile in the form of the free base, or a pharmaceutically acceptable salts and/or solvate thereof. The present invention also relates to a process for the preparation of the inventive composition, pharmaceutical formulations containing said composition and to the use of said composition either by concomitant administration or by separate administration as an improvement of the treatment of affective disorders such as depression, anxiety, obsessive compulsive disorder (OCD), etc.

BACKGROUND OF THE INVENTION

Today, it is generally considered that antidepressants take 2–4 weeks to reach full clinical effect. In contrast, the side effects occur immediately. Thus, slow onset of action of antidepressants leads to a vulnerable period for patients in which they experience the side effects, but not the therapeutic effects of drugs. There is often a heavy burden on the treating physician to persuade the patient to continue with the treatment during this period. Furthermore, in suicidal patients, as the onset of action is gradual, initiative may be regained without the experiencing of full reversal of symptoms, leaving a window of risk for suicide and a frequent requirement for hospitalization. An antidepressant with fast onset of action would not only be beneficial due to the faster symptom reduction, but would also be more acceptable to patients and physicians and reduce the need for, and duration of, hospitalization. The same long period to reach full clinical effect has been shown in the treatment of other affective disorders such as anxiety and OCD.

PRIOR ART

In WO 96/33710 is disclosed that the compound (R)-5-carbamoyl-8-fluoro-3-N,N-dicyclobutylamino-3,4-dihydro-2H-1-benzopyran, -dihydro-2H-1-benzopyran, which has high affinity to 5-HT receptors and antagonizes $5\text{-HT}_{1A}$-mediated responses, induces a rapid improvement of depressed patients treated with serotonin reuptake inhibitors.

SUMMARY OF THE INVENTION

The present invention is directed to a new composition comprising a first component (a) which is the specific $5\text{-HT}_{1A}$ antagonist (R)-5-carbamoyl-8-fluoro-3-N,N-dicyclobutylamino-3,4-dihydro-2H-1-benzopyran in the form of the free base, or a pharmaceutically acceptable salt and/or solvate thereof, and a second component (b) which is the specific 5-HT reuptake inhibitor (+)-1-[3-(dimethylamino)propyl]-1-(p-fluorophenyl)-5-phthalancarbonitrile in the form of the free base, or a pharmaceutically acceptable salt and/or solvate thereof. Said composition attains a faster onset of action and, consequently, provides a more efficacious treatment of patients suffering from affective disorders, particularly depression.

DETAILED DESCRIPTION OF THE INVENTION

It has been shown in animal studies that acute administration of selective 5-HT reuptake inhibitors (SSRIs) decreases the electrical impulse propagation in 5-HT neurones via a negative feedback reaction probably mediated by collateral 5-HT axons releasing 5-HT in raphe nuclei. By inhibiting the somatodendritic $5\text{-HT}_{1A}$ autoreceptors in the raphe nuclei, the selective antagonists counteract the decrease in propagation caused by 5-HT reuptake inhibitors. This indicates that a selective blockade of somatodendritic autoreceptor, i.e., $5\text{-HT}_{1A}$ antagonist, may have a clinical potential to improve the efficacy of 5-HT reuptake inhibitors (SSRIs) and offer a new rationale for rapid onset of effect in the treatment of affective disorders, for instance the antidepressant actions.

The compound (R)-5-carbamoyl-8-fluoro-3-N,N-dicyclobutylamino-3,4-dihydro-2H-1-benzopyran in the form of the free base, or a pharmaceutically acceptable salt and/or solvate thereof, as disclosed herein, is described in WO 95/11891, as a selective 5-HT1A receptor antagonist.

The enantiomer (+)-1-[3-(dimethylamino)propyl]-1-(p-fluorophenyl)-5-phthalancarbonitrile disclosed herein, and which is stated to be a 5-HT reuptake inhibitor, is described in U.S. Pat. No. 4,943,590.

The (R)-5-carbamoyl-8-fluoro-3-N,N-dicyclobutylamino-3,4-dihydro-2H-1-benzopyran is in the form of the free base, or a pharmaceutically acceptable salt and/or solvate thereof. Both organic and inorganic acids can be employed to form nontoxic pharmaceutically acceptable acid addition salts of the compounds of this invention. Illustrative acids are sulfuric, nitric, phosphoric, oxalic, hydrochloric, formic, hydrobromic, citric, acetic, lactic, tartaric, dibenzoyltartaric, diacetyltartaric, pamoic, ethanedisulfonic, sulfamic, succinic, propionic, glycollic, malic, gluconic, pyruvic, phenylacetic, 4-aminobenzoic, anthranilic, salicylic, 4-aminosalicylic, 4-hydroxybenzoic, 3,4-dihydroxybenzoic, 3,5-dihydroxybenzoic, 3-hydroxy-2-naphthoic, nicotinic, methanesulfonic, ethanesulfonic, hydroxyethanesulfonic, benzenesulfonic, p-toluenesulfonic, sulfanilic, naphthalenesulfonic, ascorbinic, cyclohexylsulfamic, fumaric, maleic and benzoic acids. These salts are readily prepared by methods known in the art.

(R)-5-carbamoyl-8-fluoro-3-N,N-dicyclobutylamino-3,4-dihydro-2H-1-benzopyran possesses a high affinity to the specific subgroup of $5\text{-HT}_{1A}$ receptor in the CNS and acts as an antagonist on that $5\text{-HT}_{1A}$ receptor, and also shows favorable bioavailability after oral administration.

The composition according to the present invention may exist in one pharmaceutical formulation comprising (R)-5-carbamoyl-8-fluoro-3-N,N-dicyclobutylamino-3,4-dihydro-2H-1-benzopyran in the form of the free base, or a pharmaceutically acceptable salt and/or solvate thereof, and (+)-1-[3-(dimethylamino)propyl]-1-(p-fluorophenyl)-5-phthalancarbonitrile in the form of the free base, or a pharmaceutically acceptable salt and/or solvate thereof. Alternatively, the composition may exist in two different pharmaceutical formulations, one for (R)-5-carbamoyl-8-fluoro-3-N,N-dicyclobutylamino-3,4-dihydro-2H-1- benzopyran in the form of the free base, or a pharmaceutically acceptable salt and/or solvate thereof and one for (+)-1-[3-(dimethylamino)propyl]-1-(p-fluorophenyl)-5-phthalancarbonitrile in the form of the free base, or a pharmaceutically acceptable salt and/or solvate thereof. The pharmaceutical formulation may be in the form of tablets or capsules, powders, mixtures, solutions or other suitable pharmaceutical formulation forms such as patches and nasal formulations.

The composition of the present invention can be prepared such that (R)-5-carbamoyl-8-fluoro-3-N,N-dicyclobutylamino- N-dicyclobutylamino-3,4-dihydro-2H-1-benzopyran in the form of the free base, or a pharmaceutically acceptable salt and/or solvate thereof is incorporated into the same pharmaceutical formulation as (+)-1-[3-(dimethylamino)propyl]-1-(p-fluorophenyl)-5-phthalancarbonitrile in the form of the free base, or a pharmaceutically acceptable salt and/or solvate thereof by, e.g., mixing in a conventional way.

The present invention also includes a method of improving the onset of therapeutic action by concomitant administration of a composition comprising (R)-5-carbamoyl-8-fluoro-3-N,N-dicyclobutylamino-3,4-dihydro-2H-1-benzopyran in the form of the free base, or a pharmaceutically acceptable salt and/or solvate thereof and (+)-1-[3-(dimethylamino) propyl]-1-(p-fluorophenyl)-5-phthalancarbonitrile in the form of the free base, or a pharmaceutically acceptable salt and/or solvate thereof.

A further embodiment of the present invention is a kit containing a dosage unit of (R)-5-carbamoyl-8-fluoro-3-N,N-dicyclobutylamino-3,4-dihydro-2H-1-benzopyran in the form of the free base, or a pharmaceutically acceptable salt and/or solvate thereof, and a dosage unit of (+)-1-[3-(dimethylamino)propyl]-1-(p-fluorophenyl)-5-phthalancarbonitrile in the form of the free base, or a pharmaceutically acceptable salt and/or solvate thereof, optionally with instructions for use.

PHARMACEUTICAL FORMULATIONS

According to the present invention the compounds in the composition will normally be administered orally, rectally, transdermally, nasally or by injection, in the form of pharmaceutical formulations comprising the active ingredient either as a free base; a solvate, e.g., a hydrate; or a pharmaceutically acceptable nontoxic acid addition salt, e.g., the hydrochloride, hydrobromide, lactate, acetate, phosphate, sulfate, sulfamate, citrate, tartrate, oxalate and the like in a pharmaceutically acceptable dosage form. The dosage form may be a solid, semisolid or liquid formulation. Usually the active substances will constitute between 0.1% and 99% by weight of the formulation, more specifically between 0.5 and 20% by weight for formulations intended for injection and between 0.2 and 50% by weight for formulations suitable for oral administration.

The pharmaceutical formulation comprises the active ingredients, optionally in association with adjuvants, diluents, excipients and/or inert carriers.

To produce pharmaceutical formulations of the composition of the invention in the form of dosage units for oral application, the selected compounds may be mixed with a solid excipient, e.g., lactose, saccharose, sorbitol or mannitol; starches such as potato starch, corn starch or amylopectin; cellulose derivatives; a binder such as gelatin or polyvinylpyrrolidone; disintegrants; e.g., sodium starch glycolate, cross-linked PVP and cross-caramellose sodium; a lubricant such as magnesium stearate, calcium stearate, polyethylene glycol, waxes, paraffin, and the like; and an antisticking agent such as talc or colloidal silicon dioxide, and then compressed into tablets. If coated tablets are required, the cores, prepared as described above, may be coated with a polymer known to one of skill in the art, e.g., HPMC, HC or other cellulose derivatives, or PVP, wherein the polymer is dissolved in water or a readily volatile organic solvent or mixture of organic solvents. Alternatively, the tablets can be coated with a concentrated sugar solution which may contain, e.g., gum arabic, gelatin, talcum, titanium dioxide, and the like. Dyestuffs may be added to these coatings in order, for instance, to readily distinguish between tablets containing different active substances or different amounts of the active compounds.

For the formulation of soft gelatin capsules, the active substances may be admixed with, e.g., a vegetable oil or polyethylene glycol. Hard gelatin capsules may contain granules of the active substances using any of the above mentioned excipients for tablets, e.g., lactose, saccharose, sorbitol, mannitol, starches (e.g., potato starch, corn starch or amylopectin), cellulose derivatives, plasticizers, polyetheneglycol, waxes, lipids or gelatin. Also, liquids or semisolids of the drug can be filled into hard gelatin capsules.

Dosage units for rectal application can be solutions or suspensions or can be prepared in the form of suppositories comprising the active substances in a mixture with a neutral fatty base, or gelatin rectal capsules comprising the active substances in admixture with vegetable oil or paraffin oil. Liquid formulations for oral application may be in the form of solutions, syrups or suspensions, for example solutions containing from about 0.2% to about 20% by weight of the active substances herein described, the balance being sugar and a mixture of ethanol, water, glycerol and propylene glycol. Optionally such liquid formulations may contain coloring agents, flavoring agents, saccharin and carboxymethyl cellulose as a thickening agent or other excipients known to a person skilled in the art.

Solutions for parenteral applications by injection can be prepared in an aqueous solution of a water-soluble pharmaceutically acceptable salt of the active substances, preferably in a concentration of from about 0.5% to about 10% by weight. These solutions may also contain stabilizing agents and/or buffering agents and may conveniently be provided in various dosage unit ampoules.

Suitable daily doses of the active compounds in the composition of the invention in therapeutic treatment of humans are about 0.01–100 mg/kg bodyweight for peroral administration and 0.001–100 mg/kg bodyweight for parenteral administration. The daily doses of the active ingredient (R)-5-carbamoyl-8-fluoro-3-N,N-dicyclobutylamino-3,4-dihydro-2H-1-benzopyran in the form of the free base, or a pharmaceutically acceptable salt and/or solvate thereof, may very well differ from the daily doses of the active ingredient (+)-1-[3-(dimethylamino) propyl]-1-(p-fluorophenyl)-5-phthalancarbonitrile in the form of the free base, or a pharmaceutically acceptable salt and/or solvate thereof, but the doses can also be the same for both of the active ingredients.

MEDICAL AND PHARMACEUTICAL USE

In a further aspect the present invention provides the use of the composition comprising a first component (a) which is (R)-5-carbamoyl-8-fluoro-3-N,N-dicyclobutylamino-3,4-dihydro-2H-1-benzopyran in the form of the free base, or a pharmaceutically acceptable salt and/or solvate thereof and a second component (b) which is (+)-1-[3(dimethylamino) propyl]-1-(p-fluorophenyl)-5-phthalancarbonitrile in the form of the free base, or a pharmaceutically acceptable salt and/or solvate thereof, in the treatment of 5-hydroxytryptamine-mediated disorders, such as affective disorders. Examples of affective disorders are disorders in the CNS such as mood disorders (depression, major depressive episodes, dysthymia, seasonal affective disorder, depressive phases of bipolar disorder); anxiety disorders (obsessive compulsive disorder, panic disorder with/without agoraphobia, social phobia, specific phobia, generalized anxiety disorder, posttraumatic stress disorder); personality disorders (disorders of impulse control, trichotellomania); and sleep disorders.

Other disorders in the CNS such as eating disorders (obesity, anorexia, bulimia), premenstrual syndrome, sexual disturbances, alcoholism, tobacco abuse, autism, attention deficit, hyperactivity disorder, migraine, memory disorders (age-associated memory impairment, presenile and senile dementia such as Alzheimer's disease), pathological aggression, schizophrenia, endocrine disorders (e.g., hyperprolactinaemia), stroke, dyskinesia, Parkinson's disease, thermoregulatory disorders, pain and hypertension may also be treated with the combination described herein.

Examples of other hydroxytryptamine-mediated disorders are urinary incontinence, vasospasm and growth control of tumors (e.g., lung carcinoma) and it may be possible to treat those with the combination described herein as well.

PHARMACOLOGY

Potentiation of the 5-$HT_{1A}$ autoreceptor blocking effect of 5-HT of (+)-1-[3-(dimethylamino)-propyl]-1-(p-fluorophenyl)-5-phthalancarbonitrile by (R)-5-carbamoyl-8-fluoro-3-N,N-dicyclobutylamino-3,4-dihydro-2H-1-benzopyran.

MATERIALS AND METHODS

Animals

The studies were carried out in male Sprague-Dawley rats (290–450 g; B&K Universal, Sollentuna, Sweden). The animals were housed for at least 3 weeks after arrival until used in the experiments.

Methods

The studies were carried out by means of intra-cerebral microdialysis in conscious rats. To assess any putative regional differences between dorsal and median raphe-innervated 5-HT projection areas, dialysis probes were simultaneously implanted both into the frontal cortex (FCx) and dorsal hippocampus (DH).

Microdialysis

The rats were anesthetized with a mixture of ketamine HCl (67 mg/kg intraperitoneal (IP); Ketalar®, Park-Davis) and xylazine HCl (13 mg/kg IP; Rompune®, Bayer-Leverkusen). U-shaped microdialysis probes (total dialysis fibre length 4 mm, OD 220 $\mu$m) were stereotaxically implanted in the frontal cortex (FCx) and dorsal hippocampus (DH); probe tips at AP+3.5, ML−3.0, DV−4.2 and −4.3, ML+2.5, DV−4.2, respectively, vs. bregma and dura surface (Paxinos, et al. in The Rat Brain in Stereotaxic Coordinates, $2^{nd}$ Ed., Academic Press, San Diego (1996)). The microdialysis studies were performed in conscious animals after a 40–48 h recovery period, during which they were kept individually. Food and water were allowed ad libitum in the plastic cages subsequently used in the experimental sessions. On the day of the experiment, the probe inlets were connected to a syringe perfusion pump (CMA/100; CMA Microdialysis AB, Sweden), delivering artificial CSF (Hjorth, S., J. Neurochem. 60:776–779 (1993)) at a speed of 1.3 $\mu$l/min. Twenty-min dialysate fractions were collected from the probe outlet tubing, and immediately analyzed for 5-HT and 5-HIAA by standard HPLC-EC methods. After the perfusion was commenced, a period of 2–3 h was allowed to establish stable baseline dialysate levels of 5-HT prior to drug treatment(s).

We claim:

1. A composition comprising a first component (a) which is (R)-5-carbamoyl-8-fluoro-3-N,N-dicyclobutylamino-3,4-dihydro-2H-1-benzopyran in the form of the free base, or a pharmaceutically acceptable salt and/or solvate thereof, and a second component (b) which is (+)-1-[3-(dimethylamino) propyl]-1-(p-fluorophenyl)-5-phthalancarbonitrile in the form of the free base, or a pharmaceutically acceptable salt and/or solvate thereof.

2. A method for the treatment of 5-HT-mediated disorders, which comprises administering to a patient suffering therefrom the composition according to claim 1.

3. The method according to claim 2 for the treatment of affective disorders.

4. The method according to claim 3 for the treatment of mood disorders.

5. The method according to claim 4 for the treatment of depression.

6. A method of decreasing the period of time before the onset of therapeutic action of (+)-1-[3-(dimethylamino) propyl]-1-(p-fluorophenyl)-5-phthalancarbonitrile in a patient in need thereof, which comprises concomitantly administering to the patient the composition according to claim 1.

7. A pharmaceutical formulation wherein the active ingredients are the components in the composition according to claim 1, optionally in association with adjuvants, excipients and/or inert carriers.

8. A pharmaceutical formulation according to claim 7 wherein the first component (a) is concomitantly administered with the second component (b).

9. A process for the preparation of the composition according to claim 1 wherein the first component (a) is incorporated into the same pharmaceutical formulation as the second component (b).

10. A process for the preparation of the composition according to claim 1 wherein the first component (a) is in one pharmaceutical formulation and is combined with the second component (b) in a different pharmaceutical formulation.

11. A kit containing a dosage unit of a first component (a) which is (R)-5-carbamoyl-8-fluoro-3-N,N-dicyclobutylamino-3, 4-dihydro-2H-1-benzopyran in the form of the free base, or a pharmaceutically acceptable salt and/or solvate thereof, and a dosage unit of a second component (b) which is (+)-1-[3-(dimethylamino)propyl]-1-(p-fluorophenyl)-5-phthalancarbonitrile in the form of the free base, or a pharmaceutically acceptable salt and/or solvate thereof, optionally with instructions for use.

* * * * *